United States Patent [19]

Rakhit et al.

[11] 4,333,937

[45] Jun. 8, 1982

[54] 2-(PIPERAZINYL)-4-PYRIMIOINAMINES

[75] Inventors: Sumanas Rakhit, Dollard des Ormeaux; Jehan F. Bagli, Kirkland, both of Canada

[73] Assignee: American Home Products Corp., New York, N.Y.

[21] Appl. No.: 141,548

[22] Filed: Apr. 18, 1980

[51] Int. Cl.$^3$ .................................................. A61K 31/505
[52] U.S. Cl. ............................. 424/251; 260/243.3; 544/284; 544/291; 544/295
[58] Field of Search ............... 424/251; 544/284, 291, 544/295; 260/243.3

[56] References Cited

U.S. PATENT DOCUMENTS

| | | | |
|---|---|---|---|
| 3,511,836 | 5/1970 | Hess | 544/291 |
| 3,935,213 | 1/1976 | Hess | 544/291 |
| 4,001,237 | 1/1977 | Partyka et al. | 544/284 |
| 4,093,726 | 6/1978 | Winn et al. | 424/250 |

OTHER PUBLICATIONS

Althuis et al., J. Med. Chem., 20, 146–149 (1977).
Derwent Publications Ltd., Farmdoe 36461B for Netherland Patent 7,804,135.

Primary Examiner—Paul M. Coughlan, Jr.
Attorney, Agent, or Firm—Arthur E. Wilfond

[57] ABSTRACT

Herein is disclosed 2-(1-piperazinyl)-4-pyrimidinamine derivatives, acid addition salts thereof, processes for their preparation, methods of using the derivatives and pharmaceutical compositions of the derivatives. The derivatives are distinguished most readily by having novel substituents at position 4 of the piperazinyl radical, the substituents being selected from the group consisting of optionally substituted 2-cycloheptimidazolyl, 1,4,5,6,7,8-hexahydrocycloheptimidazol-2-yl, 2-benzoxazolyl, benzthiazol-2-yl, 1H-2-benzimidazolyl and 1-oxo-2,4,6-cycloheptarien-2-yl. The derivatives are useful for treating hypertension in a mammal.

18 Claims, No Drawings

2-(PIPERAZINYL)-4-PYRIMIOINAMINES

BACKGROUND OF THE INVENTION

This invention relates to novel 2-(1-piperazinyl)-4-pyrimidinamine derivatives, to therapeutically acceptable acid addition salts thereof, to processes for their preparation, to methods of using the derivatives and to pharmaceutical compositions of the derivatives. These derivatives are useful for treating hypertension in mammals.

The applicants are aware of the piperazine derivatives are exemplified by T. H. Althuis and H.-J. Hess, J. Med. Chem., 20, 146 (1977); R. A. Partyka and R. R. Crenshaw, U.S. Pat. No. 4,001,237, issued Jan. 4, 1977; H.-J. E. Hess, U.S. Pat. No. 3,511,836, issued May 12, 1970; Derwent Publications Ltd., Farmdoc 36461 B for Netherland Pat. No. 7,804,135; H.-J. E. Hess, U.S. Pat. No. 3,935,213, issued Jan. 27, 1976; and M. Winn and J. Kynel, U.S. Pat. No. 4,093,726, issued June 6, 1978 as being the most closely related compounds to the compounds of this invention. However, the reported compounds lack the substituents on the piperazine and/or pyrimidinamine rings which are characteristic of the compounds of this invention.

SUMMARY OF THE INVENTION

The compounds of this invention are represented by formula I

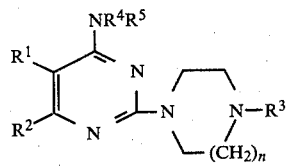

(I)

in which $R^1$ and $R^2$ are hydrogen, or $R^1$ and $R^2$ together form a chain of the formula

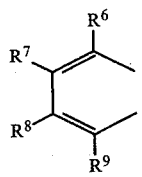

wherein $R^6$, $R^7$, $R^8$ and $R^9$ each is hydrogen or lower alkoxy; $R^3$ is selected from the group consisting of

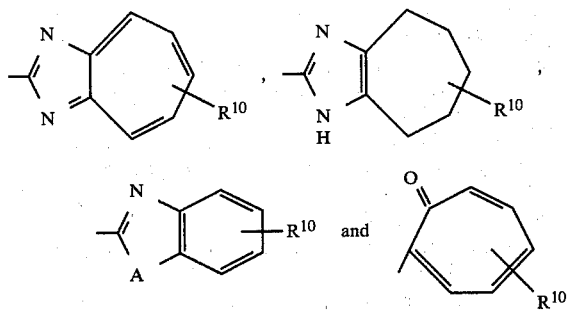

wherein $R^{10}$ is hydrogen or at least one substituent selected from halo, lower alkyl, lower alkoxy, hydroxy, 1-oxo(lower)alkoxy or $NR^{11}R^{12}$ wherein $R^{11}$ and $R^{12}$ each is hydrogen or lower alkyl; A is O, S or NH; $R^4$ and $R^5$ each is hydrogen or lower alkyl; and n is 1 or 2; or a therapeutically acceptable acid addition salt thereof.

A preferred group of compounds of this invention is represented by formula I in which $R^1$ and $R^2$ are hydrogen, or $R^1$ and $R^2$ together form a chain of the formula

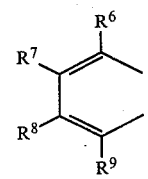

wherein $R^6$, $R^7$, $R^8$ and $R^9$ each is hydrogen or lower alkoxy; $R^3$ is selected from the group consisting of

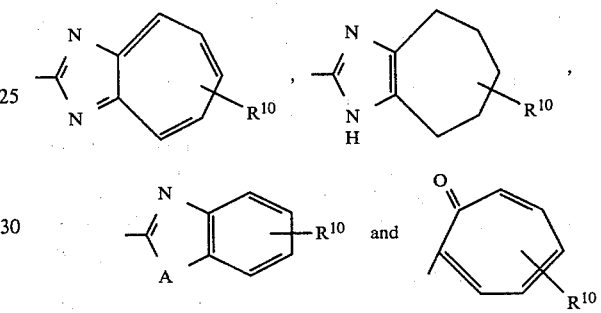

wherein $R^{10}$ is hydrogen, halo, lower alkyl, lower alkoxy, hydroxy, 1-oxo(lower)-alkoxy or $NR^{11}R^{12}$ wherein $R^{11}$ and $R^{12}$ each is hydrogen or lower alkyl; A is O, S or NH; $R^4$ and $R^5$ each is hydrogen or lower alkyl; and n is 1 or 2; or a therapeutically acceptable acid addition salt thereof.

A more preferred group of compounds of this invention is represented by formula Ia

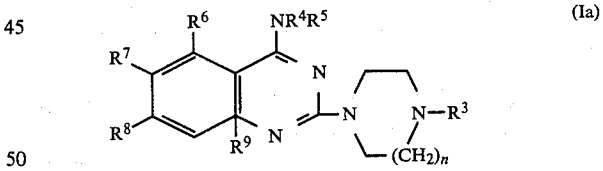

(Ia)

in which $R^4$, $R^5$ and $R^6$ are hydrogen, $R^7$ and $R^8$ each is lower alkoxy, $R^9$ is hydrogen or lower alkoxy, $R^3$ is selected from the group consisting of

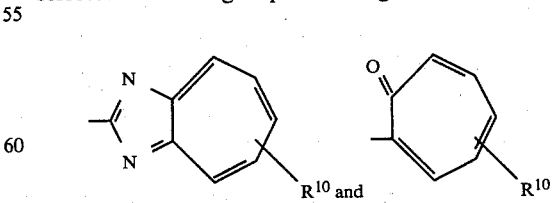

wherein $R^{10}$ is hydrogen, halo or lower alkoxy; and n is 1; or a therapeutically acceptable acid addition salt thereof.

A most preferred group of compounds of this invention is represented by formula Ia in which $R^4$, $R^5$ and $R^6$ are hydrogen, $R^7$ and $R^8$ each is lower alkoxy, $R^9$ is hydrogen or lower alkoxy, $R^3$ is selected from the group consisting of

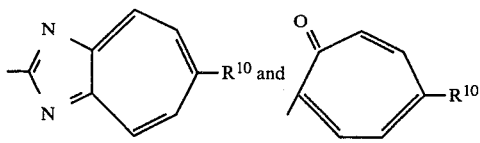

wherein $R^{10}$ is hydrogen, chloro or lower alkoxy; and n is 1; or a therapeutically acceptable acid addition salt thereof.

A pharmaceutical composition is provided by combining the compound of formula I, or a therapeutically acceptable acid addition salt thereof, and a pharmaceutically acceptable carrier.

The compounds of this invention can be used to treat hypertension in a hypertensive mammal by administering to the mammal an effective antihypertensive amount of a compound of formula I or a therapeutically acceptable acid addition salt thereof.

DETAILED DESCRIPTION OF THE INVENTION

The term "lower alkyl" as used herein means straight chain alkyl radicals containing from one to six carbon atoms and branched chain alkyl radicals containing from three to four carbon atoms and includes methyl, ethyl, propyl, 1-methylethyl, butyl, 1,1-dimethylethyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, 1-methylethoxy, butoxy, hexanoxy and the like.

The term "halo" as used herein means halogens and includes fluorine, chlorine, bromine and iodine, unless stated otherwise.

The term "1-oxo(lower)alkoxy" as used herein means straight chain 1-oxoalkoxy radicals containing from two to six carbon atoms and branched chain 1-oxoalkoxy radicals containing four to six carbon atoms and includes acetyloxy, 1-oxopropoxy, 1-oxobutoxy, 2,2-dimethyl-1-oxopropoxy, 1-oxohexoxy and the like.

The term "lower alkanol" as used herein means both straight and branched chain alkanols containing from one to four carbon atoms and includes methanol, ethanol, 1-methylethanol, butanol and the like.

The term "organic proton acceptor" as used herein means the organic bases or amines, for instance, triethylamine, pyridine, N-ethylmorpholine, 1,5-diazabicyclo[4.3.0]non-5-ene and the like.

The term "inorganic proton acceptor" as used herein means the inorganic bases, preferably the alkali methyl hydroxides, carbonates and bicarbonates, for example, sodium hydroxide, potassium hydroxide, sodium carbonate, sodium bicarbonate, potassium carbonate and the like.

The term "proton acceptor" as used herein means a proton acceptor selected from an organic proton acceptor and inorganic proton acceptor, as defined hereinabove.

The compounds of this invention are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture.

These salts, when administered to a mammal, possess the same pharmacologic activities as the corresponding bases. For many purposes it is preferable to administer the salts rather than the base compounds. Suitable acids to form these salts include the common mineral acids, e.g. hydrohalic, sulfuric or phosphoric acid; the organic acids, e.g. maleic, citric or tartaric acid; and acids which are sparingly soluble in body fluids and which impart slow-release properties to their respective salts, e.g. pamoic or tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The antihypertensive effect of the compounds of formula I or a therapeutically acceptable acid addition salt thereof is demonstrated in standard pharmacological tests, for example, in tests conducted in the spontaneously hypertensive rat (SHR) such as described by I. Varva, et al., Can. J. PHysiol. Pharmacol., 51, 727 (1973). The latter test method is modified in the following manner: Male rats, Okamota-Aoki Strain, ranging in weight between 250–400 g were anesthetized with diethyl ether. Their left femoral arteries and veins were cannulated with polyethylene tubing of the appropriate size. Each animal was then enfolded in a rubber mesh jacket which was secured with 4 towel clamps. The animal was suspended via the towel clamps from a bar and allowed to recover from the anesthesia. The femorial arterial cannula was connected to a Stratham pressure transducer (Model P23, Gould Stratham Instruments, Hato Rey, Porto Rico), which in turn was attached to a polygraph for recording arterial pressure and pulse rate. The pulse rate was considered to be the heart rate.

When the blood pressure (BP) had stabilized (usually two hours after cessation of the anesthesia) the intravenous injection of the standard agonists was begun. Each of the 4 agonists was prepared from concentrated, refrigerated, stock solutions to be delivered in a volume of 1 ml/kg. The doses given were: isoproterenol 0.5 $\mu g/kg$, adrenalin 2.0 $\mu g/kg$, tyramine 200 $\mu g/kg$ and angiotensin I 0.25 $\mu g/kg$. The agonists were usually given in random order except that tyramine was never preceded by isoproterenol as the response to tyramine seemed to be blunted after a prior injection of isoproterenol. Enough time was allowed for the BP to return to preinjection levels before the next agonist was given. After the last agonist was given the test compound was administered by gastric gavage in a volume of 5 ml/kg. Heart rate and blood pressure were noted at 5, 10, 15, 30, 45 and 60 minutes and hourly thereafter for a period of at least 4 hours after drug administration. At 1 and 2 hours post-drug, the agonists were again injected at the same concentration and in the same order as during the control period.

Using this method, the following representative compounds of formula I are effective for reducing the blood pressure (BP) in the spontaneously hypertensive rat (the amount of test compound and its reduction in BP are indicated in the parentheses): 2-[4-(2-cycloheptimidazolyl)-1-piperazinyl]-6,7-dimethoxy-4-quinazolinamine (described in Example 2, at a dose of 1.0 mg/kg of body weight causes a 20% decrease in mean BP at 3 hours), 2-[4-(6-chloro-2-cycloheptimidazolyl)-1-piperazinyl]-6,7-dimethoxy-4-quinazolinamine (described in Example 2, at a dose of 5.0 mg/kg of body weight causes a 18% decrease in mean BP at 3 hours), 2-[4-(2-cycloheptimidazolyl)-1-piperazinyl]-4-pyrimidinamine (described in Example 2, at a dose of 50 mg/kg of body weight causes a 16% decrease in mean BP at 3 hours), 2-[4-(4-amino-6,7-dimethoxy-2-quinazolinyl)-1-piperazinyl-2,4,6-cycloheptatrien-1-one (described in Example 3, at a dose of 1.0 mg/kg of body weight causes a 28% decrease in mean BP at 1 hour), 5-chloro-2-[4-(4-amino-6,7-dimethoxy-2-quinazolinyl)-1-piperazinyl]-2,4,6-cycloheptatrien-1-one (described in Example 3, at a dose of 10 mg/kg of body weight causes a 19% decrease in mean BP at 1 hour), 2-[4-(2-cycloheptimidazolyl)-1-piperazinyl]-6,7,8-trimethoxy-4-quinazolinamine (described in Example 4, at a dose of 2.5 mg/kg of body weight causes a 21% decrease in mean BP at 1 hour), 2-[4-(6-ethoxy-2-cycloheptimidazolyl)-1-piperazinyl]-6,7-dimethoxy-4-quinazolinamine (described in Example 5, at a dose of 5.0 mg/kg of body weight causes a 19% decrease in mean BP at 3 hours), 2-[4-(benzthiazol-2-yl)-1-piperazinyl]-6,7-dimethoxy-4-quinazolinamine (described in Example 6, at a dose of 0.1 mg/kg of body weight causes a 16% decrease in mean BP at 4 hours) and 2-[4-(2-cycloheptimidazolyl)-1-piperazinyl]-5,6,7-trimethoxy-4-quinazolinamine dihydrochloride (described in Example 9, at a dose of 2.5 mg/kg of body weight causes a 14% decrease in mean BP at 4 hours).

The compounds of formula I of this invention are used alone or in combination with pharmacologically acceptable carriers, the proportion of which is determined by the solubility and chemical nature of the compound, chosen route of administration and standard biological practice. For example, they are administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective antihypertensive amount of the compounds for oral administration usually ranges from about 0.01 to 200 mg per kilogram body weight per day in single or divided doses although as aforementioned variations will occur. However, a dosage level that is in the range of from about 0.05 to 100 mg per kilogram body weight per day in single or divided doses is employed most desirably for oral administration in order to achieve effective results.

The compound of formula I also can be used to produce beneficial effects in the treatment of hypertension, peripheral and cerebral vascular diseases and related disorders when combined with a second therapeutic agent comprising a therapeutically effective amount of a diuretic and/or antihypertensive agent commonly used in antihypertensive therapy. Such diuretic and/or antihypertensive therapeutic agents include, for example, the thiazide diuretics for instance, chlorothiazide or hydrochlorothiazide; mineralocorticoid antagonizing diuretic agents, e.g., spironolactone; and other diuretics such as triamtexene and furosemide. Examples of still other suitable antihypertensive agents are prazosine, hydralazine and centrally active antihypertensive agents such as methyldopa, clonidine, and reserpine; as well as the β-adrenergic blocking agents, for instance, propranolol. The compound of formula I can be administered sequentially or simultaneously with the antihypertensive and/or diuretic agent. Preferred antihypertensive and/or diuretic therapeutic agents are the antihypertensive agents such as the thiazides, mineralocorticoid antagonizing diuretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physician Desk Reference", 33 ed., Medical Economics Co., Oradell, N.J., U.S.A., 1979. For example, the agent propanolol is administered daily to humans in a range of 80 to 640 mg, usually in the form of unit doses of 10, 20, 40 or 80 mg. When used in combination, the compound of formula I is administered as described previously.

PROCESS

Reaction scheme 1 illustrates a method for preparing the compounds of formula I.

REACTION SCHEME 1

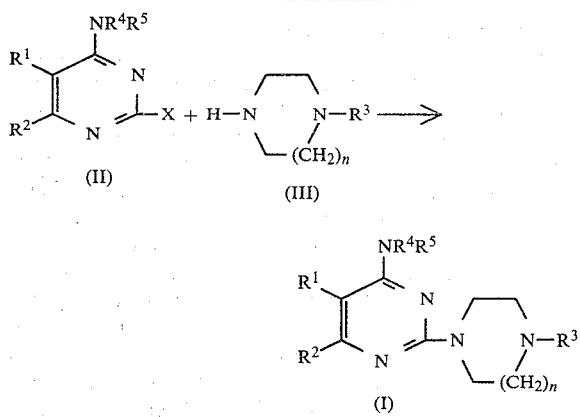

With reference to reaction scheme 1, a compound of formula II, in which $R^1$, $R^2$, $R^4$ and $R^5$ are as defined herein and X is bromo or chloro, is condensed with a compound of formula III, in which n and $R^3$ are as defined herein. Preferably, the compound of formula II is condensed with about one molar equivalent of the compound of formula III in the presence of at least one molar equivalent of a proton acceptor, preferably an organic proton acceptor. Any organic solvent which does not interfere with the condensation can be used. A preferred solvent is selected from lower alkanols, especially butanol. Also, an excess of the organic proton acceptor can serve as the solvent without the addition of another organic solvent. The condensation of the compound of formula II and the compound of formula III is usually achieved at about 75° to 150° C., preferably about 100° to 130° C., for about two to 30 hours. The corresponding compound of formula I is then isolated from the reaction mixture by conventional methods, for example, evaporation, filtration, extraction, chromatography and/or crystallization.

The starting materials of formula II are either described in the chemical literature or can be readily prepared by using analogous methods which are described, for example, the above cited article by T. H. Althuis and H.-J. Hess, J. Med. Chem., 20, 146 (1977) and H.-J. Hess, U.S. Pat. No. 3,769,286, issued Oct. 30, 1973.

A method of preparing a starting material of formula III is illustrated in reaction scheme 2.

REACTION SCHEME 2

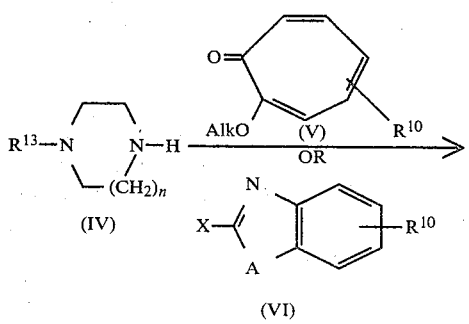

-continued
REACTION SCHEME 2

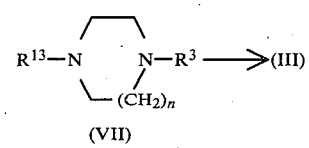

Condensation of the compound of formula IV in which n is as defined herein and $R^{13}$ is an amino protecting group, for instance, benzyl, formyl, tert-butoxycarbonyl and the like, preferably formyl, with about one molar equivalent of the compound of formula V in which $R^{10}$ is as defined herein and Alk is lower alkyl gives the corresponding compound of formula VII in which n and $R^{13}$ are as defined herein and $R^3$ is

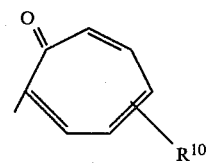

wherein $R^{10}$ is as defined herein. The condensation is readily effected by heating a solution of the compound of formula IV and V in an inert organic solvent, for example, a lower alkanol, benzene, chloroform, acetonitrile, toluene and the like, preferably a lower alkanol, at 50° to 100° C. for 10 to 60 hours and isolating the corresponding compound of formula VII.

A number of 2-alkoxy-tropones of formula V suitable as starting materials are described in various reports; for example, see the review on tropone derivatives, their preparation and their interconversions by F. Pietra, Chem. Rev., 73, 293 (1973). Thus, the 2-alkoxy-tropones are either known or can be prepared by conventional means.

The intermediates of formula VII in which n and $R^{13}$ are as defined herein and $R^3$ is

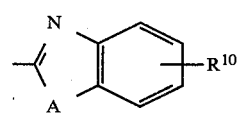

wherein A and $R^{10}$ are as defined herein are obtained by condensing the corresponding compound of formula IV in which n and $R^{13}$ are as defined herein with the corresponding compound of formula VI wherein A and $R^{10}$ are as defined herein and X is mercapto bromo or chloro, in the same manner as described above for the condensation of the compound of formula II and the compound of formula III.

The starting materials of formula VI are either described or can be prepared by analogous methods, for example, such methods are described by D. S. Jones et al., J. Chem. Soc., 4393 (1965); Chem. Abstr. 41, 754 b (1947) for M. Colonna, Pubbl. ist. chim. univ. Bologna, No. 2, 3 (1943); Derwent Publications Ltd., Farmdoc 55609A for Japanese Patent No. 3,071,088; and M. Winn and J. Kyncl, U.S. Pat. No. 4,093,726, issued June 6, 1978, referred to above.

Reaction scheme 3 illustrates a method for preparing another compound of formula III.

REACTION SCHEME 3

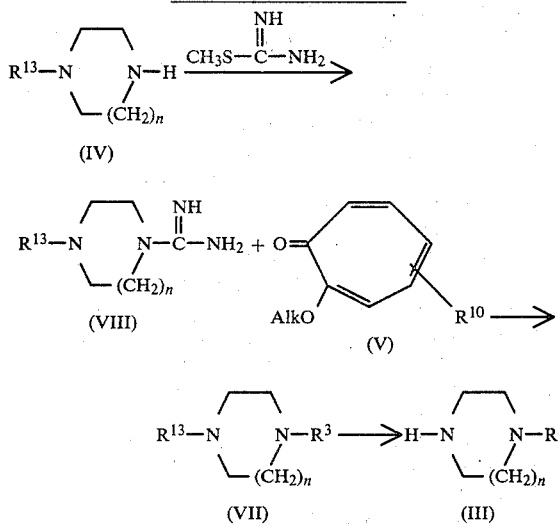

Reaction of the compound of formula IV in which n and $R^{13}$ are as defined herein with the hydroiodide salt of methylthiocarboximidamide in ethanol at about 20° to 100° C. for about two to 30 hours gives the corresponding compound of formula VIII in which n and $R^{13}$ are as defined herein. Subsequent condensation of the compound of formula VIII with about a molar equivalent of the compound of formula V in which Alk and $R^{10}$ are as defined herein in the presence of about 1.0 to 1.5 molar equivalents of sodium ethoxide affords the corresponding compound of formula VII in which n and $R^{13}$ are as defined herein and $R^3$ is

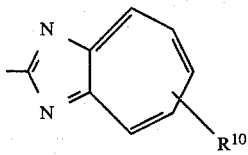

wherein $R^{10}$ is as defined herein. This condensation is achieved using ethanol as solvent and at 60° to 100° C. for one to five hours.

Removal of the amino protecting group ($R^{13}$) from the compound of formula VII in which n, $R^3$ and $R^{13}$ are as defined herein using conventional methods, for example, the formyl protecting group is easily removed with a solution of hydrogen chloride in ethanol at 20° to 100° C. for 5 to 30 hours, gives the corresponding compound of formula III.

Reduction of the compound of formula VII or formula III in which $R^3$ is

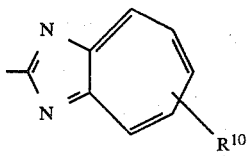

and $R^{13}$ and n are as defined herein gives the corresponding compound of formula VII or formula III, respectively, in which $R^3$ is

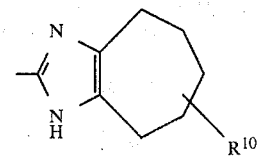

and $R^{13}$ and n are as defined herein. A preferred method of achieving this reduction is hydrogenation in the presence of a catalytic amount of rhodium on carbon in a lower alkanol, preferably methanol, at 20° to 30° C.

Still another method for preparing the compounds of formula I in which n, $R^1$, $R^2$, $R^3$, $R^4$ and $R^5$ are as defined herein makes use of the condensation of a compound of formula IX in which n, $R^1$, $R^2$, $R^4$ and $R^5$ are as

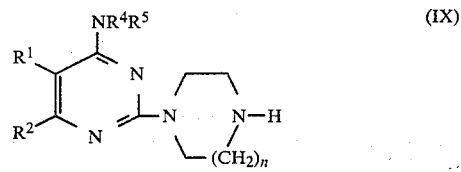

defined herein with a compound of formula V in which Alk and $R^{10}$ are as defined herein, or with a compound of formula VI in which A, $R^{10}$ and X are as defined herein, or with a compound of formula X

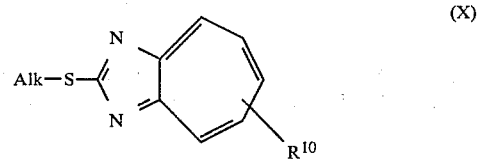

in which $R^{10}$ is as defined herein and Alk is lower alkyl. The condensation of the compound of formula IX with the compound of formula V or the compound of formula VI is conducted in the same manner as the above described for the condensation of the compound of formula IV with the compound of formula V or the compound of formula VI, respectively. Also, the condensation of the compound of formula IX with the compound of formula X is conducted in the same manner as described above for the condensation of the compound of formula IV with the compound of formula V.

The above intermediates of formula IX are prepared by first condensing the compound of formula II in which $R^1$, $R^2$, $R^4$, $R^5$ and X are as defined herein with the compound of formula IV in which n and $R^{13}$ are as defined herein, in the same manner as described above for the condensation of the compounds of formulae II and III, to obtain the corresponding compound of formula XI in in which n, $R^1$, $R^2$, $R^4$, $R^5$ and $R^{13}$ are as

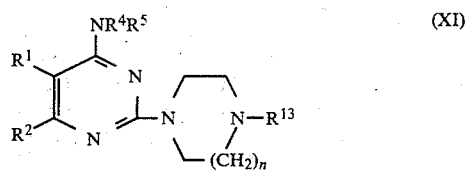

defined herein. Removal of the amino protecting group ($R^{13}$) from the compound of formula XI, in the same manner as described above for the compound of formula VII, gives the corresponding compound of formula IX in which n, $R^1$, $R^2$, $R^4$ and $R^5$ are as defined herein.

The 2-(methylthio)cycloheptimidazole of formula X in which $R^{10}$ is hydrogen and Alk is methyl is described by T. Nozoe et al., Proc. Japan Acad., 30, 482 (1954); other compounds of formula X can be prepared in a similar manner.

If desired, a compound of formula I can be converted to another compound of formula I. For example the compound of formula I in which $R^3$ is

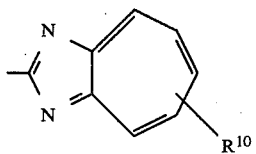

is reduced, in the same manner as described above, to obtain the corresponding compound of formula I in which $R^3$ is

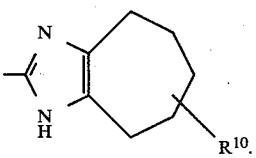

In another conversion, the compound of formula I in which n, $R^1$, $R^2$, $R^4$ and $R^5$ are as defined herein and $R^3$ is

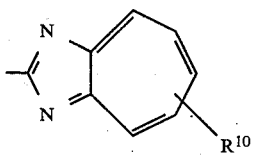

wherein $R^{10}$ is chloro is reacted with one to five molar equivalents of a sodium lower alkoxide at 20° to 100° C. for one to ten hours to obtain the corresponding compound of formula I in which n, $R^1$, $R^2$, $R^4$ and $R^5$ are as defined herein and $R^3$ is as defined immediately above wherein $R^{10}$ is lower alkoxy.

The following examples illustrate further this invention.

EXAMPLE 1

2-(1-Piperazinyl)cycloheptimidazole(III: n=1 and $R^3$=2-cycloheptimidazolyl)

A solution of 1-formylpiperazine (50 g) and methylthiocarboximidamide hydroiodide (105 g) in ethanol (250 ml) was refluxed for one hr and allowed to stir at room temperature for 18 hr. The precipitate was collected, washed with diethyl ether and dried to give 4-formyl-1-piperazincarboximidamide hydroiodide (90 g): mp 219°–225° C. and Anal. Calcd for $C_6H_{12}N_4O \cdot HI$: C, 25.37% H, 4.61% N, 19.72% and Found: C, 24.73% H, 4.55% N, 20.64%.

A mixture of the latter compound (77 g) in ethanol (100 ml) and 184 ml of a solution of sodium ethoxide, prepared from sodium (8 g) in ethanol (250 ml), was stirred for 15 min and a solution of 2-methoxy-2,4,6-cycloheptatrien-1-one (40 g) in ethanol (200 ml) was added dropwise over a period of 30 min. The resulting mixture was refluxed for 1.5 hr, cooled and filtered. The filtrate was concentrated to a small volume and poured into ice-water. The mixture was extracted with ethyl acetate and the organic extract was washed with water, dried over sodium sulfate, filtered and evaporated. The residue was crystallized from hexane-ethyl acetate to give 38.5 g of 4-(cycloheptimidazol-2-yl)-1-piperazinecarboxaldehyde: mp 170°–173° C.; nmr (DMSO-$d_6$) δ 3.5 (m, 4H), 3.9 (m, 4H), 7.8 (m, 5H) and 8.1 (s, 1H); and Anal. Calcd for $C_{13}H_{14}N_4O$: C, 64.45% H, 5.82% N, 23.12% and Found: C, 64.11% H, 5.91% N, 23.07%.

In the same manner, but replacing 2-methoxy-2,4,6-cycloheptatrien-1-one with an equivalent amount of 5-chloro-2-methoxy-2,4,6-cycloheptatrien-1-one, there was obtained 4-(6-chloro-cycloheptimidazol-2-yl)-1-piperazinecarboxaldehyde: mp 228°–229° C. (crystallized from methanol); nmr (CDCl$_3$) δ 3.6 (m, 4H), 4.0 (m, 4H), 7.85 (m, 4H) and 8.1 (s, 1H); ir (CHCl$_3$) 1670, 1605, 1560 and 1515 cm$^{-1}$; and Anal. Calcd for $C_{13}H_{13}ClN_4O$: C, 56.41% H, 4.73% N, 20.24% and Found: C, 56.50% H, 4.84% N, 20.55%.

A solution of 4-(cycloheptimidazol-2-yl)-1-piperazinecarboxaldehyde (38 g) in a solution of 500 ml of 2 N hydrogen chloride in ethanol was refluxed for 6 hr and allowed to stand at room temperature for 18 hr. The precipitate was collected and dried to give the title compound as the hydrochloride salt (31 g): mp>280° C. and nmr (DMSO-$d_6$) δ 3.37 (t, 4H), 4.3 (t, 4H), 8.4 (m, 5H) and 10.0 (s, 2H).

In the same manner, but replacing 4-(cycloheptimidazol-2-yl)-1-piperazinecarboxaldehyde with an equivalent amount of 4-(6-chloro-cycloheptimidazol-2-yl)-1-piperazinecarboxaldehyde, there was obtained 6-chloro-2-(1-piperazinyl)cycloheptimidazole hydrochloride: mp 210° C. (crystallized from methanol-acetone) and nmr (DMSO-$d_6$) δ 3.30 (4H), 4.07 (4H), 7.73 (d, 2H), 8.27 (d, 2H) and 9.65 (1H).

EXAMPLE 2

2-[4-(2-Cycloheptimidazolyl)-1-piperazinyl]-6,7-dimethoxy-4-quinazolinamine (Ia: $R^3$=2-cycloheptimidazolyl; $R^4$, $R^5$, $R^6$ and $R^9$=H; $R^7$ and $R^8$=OMe; and n=1)

A mixture of 2-(1-piperazinyl)cycloheptimidazole hydrochloride (4.53 g, described in Example 1) and triethylamine (3.64 g) in butanol (500 ml) was stirred for one hr and 2-chloro-4-amino-6,7-dimethoxyquinazoline [4.35 g, prepared as described by T. H. Althius and H.-J. Hess, J. Med. Chem., 20, 146 (1977)] was added. The mixture was refluxed for 18 hr. The resulting precipitate was collected on a filter. The filtrate was evaporated to dryness. A suspension of the precipitate and the evaporated filtrate in a cold, aqueous solution of sodium bicarbonate (5% w/v) was stirred for 30 min and filtered. The precipitate was washed with water, air-dried and crystallized from methanol-dichloromethane to give the title compound (6.3 g): mp 294°–296° C.; ir (nujol mull) 3300, 3180, 1650, 1625, 1598 and 1560 cm$^{-1}$; uv max (MeOH) 251 nm (ε=63670); nmr (DMSO-$d_6$) δ 3.85 (m, 14H) and 7.4 (m, 7H); and Anal. Calcd for $C_{22}H_{23}N_7O_2$:

C, 63.29% H, 5.55% N, 23.49% and Found: C, 62.96% H, 5.60% N, 23.61%.

To a hot solution of 1.27 g of maleic acid in 200 ml methanol, 4.17 g of the title compound (finely powdered) was added in portions with constant stirring. The solution was filtered and cooled to room temperature. The crystalline solid was filtered and air dried to give 4 g of the maleate salt of the title compound. The filtrate was concentrated to half the volume and 250 ml of diethyl ether was added. The yellow precipitate was collected and dried to yield another 1.0 g of the maleate salt of the title compound, which was crystallized from methanol: mp 189°–193° C.; ir (nujol mull) 3330, 3160 and 1593 cm$^{-1}$; uv max (MeOH) 252 ($\epsilon$=64,500) and 360 nm ($\epsilon$=25,400); nmr (DMSO-d$_6$) $\delta$ 3.84 (s, 3H), 3.90 (s, 3H), 4.02 (m, 8H), 6.08 (s, 2H), 7.6 (m, 7H) and 8.65 (s, 2H); and Anal. Calcd for $C_{22}H_{23}N_7O_2 \cdot C_4H_4O_4 \cdot 2\text{-}H_2O$: C, 54.83% H, 5.44% N, 17.22% and Found: C, 54.40% H, 5.09% N, 16.88%.

Similarly, by replacing 2-(1-piperazinyl)cycloheptimidazole with an equivalent amount of 6-chloro-2-(1-piperazinyl)cycloheptimidazole, described in Example 1, there was obtained 2-[4-(6-chloro-2-cycloheptimidazolyl)-1-piperazinyl]-6,7-dimethoxy-4-quinazolinamine hydrochloride (Ia: $R^3$=6-chloro-2-cycloheptimidazolyl, $R^4$, $R^5$, $R^6$ and $R^9$=H, $R^7$ and $R^8$=OMe, and n=1) mp >250° C. (crystallized from methanol); ir (nujol mull) 3350 and 1200 cm$^{-1}$); uv max (MeOH) 311 ($\epsilon$=7350) and 252 nm ($\epsilon$=64300); nmr (DMSO-d$_6$) $\delta$ 3.8 (3H), 3,85 (3H), 3.95 (m, 8H), 6.95 (1H), 7.5 (1H) and 7.9 (m, 4H); and Anal. Calcd for $C_{22}H_{22}ClN_7O_2 \cdot HCl$: C, 54.15% H, 4.71% N, 20.10% and Found: C, 53.77% H, 4.77% N, 19.96%.

Similarly, by condensing 2-(1-piperazinyl)cycloheptimidazole with 2-chloro-4-aminopyrimidine, there was obtained 2-[4-(2-cycloheptimidazolyl)-1-piperazinyl]-4-pyrimidinamine (I: $R^1$, $R^2$, $R^4$ and $R^5$=H; $R^3$=2-cycloheptimidazolyl; and n=1) as the di-(Z)-2-butenedioate salt. (2.0 g), mp 205°–208° C. (crystallized from methanol-diethyl ether); and Anal. Calcd for $C_{16}H_{17}N_7 \cdot 2C_4H_4O_4$: C, 53.43% H, 4.63% N, 18.18% and Found: C, 53.66% H, 4.81% N, 18.34%.

EXAMPLE 3

2-[4-(4-Amino-6,7-dimethoxyquinazolin-2-yl)-1-piperazinyl]-2,4,6-cycloheptatrien-1-one (Ia: $R^3$=1-oxo-2,4,6-cycloheptatrien-2-yl; $R^4$, $R^5$, $R^6$ and $R^9$=H; $R^7$ and $R^8$=OMe; and n=1)

A suspension of 2-(1-piperazinyl)-4-amino-6,7-dimethoxyquinazoline (2.48 g, prepared as described by T. H. Althuis and H.-J. Hess, J. Med. Chem., cited above), triethylamine (2.3 g) in butanol (190 ml) was stirred at room temperature for 2 hr and 2-methoxy-2,4,6-cycloheptatrien-1-one (2.06 g) was added. The mixture was refluxed for 48 hr, evaporated and chromatographed through silica gel using dichloromethane-methanol (9:1). The appropriate fractions were evaporated to give 1.73 g of the title compound. The latter material was stirred for 2 hr in a solution of hydrogen chloride in methanol and evaporated. The residue was crystallized from dichloromethane-methanol to give the title compound as the hydrochloride salt (0.835 g): mp 220°–224° C.; uv max (MeOH) 246 ($\epsilon$=51740) and 343 nm ($\epsilon$=25525); nmr (DMSO-d$_6$) $\delta$ 3.55 (m, 4H), 3.85 (s, 6H), 4.05 (m, 4H), 7.0 (m, 5H), 7.75 (s, 1H) and 7.85 (s, 1H); and Anal. Calcd for $C_{21}H_{23}N_5O_3 \cdot HCl$: C, 58.66% H, 5.63% N, 16.29% and Found: C, 57.62% H, 5.50% N, 16.38% H$_2$O, 1.86%.

Similarly, by replacing 2-methoxy-2,4,6-cycloheptatrien-1-one with an equivalent amount of 5-chloro-2-methoxy-2,4,6-cycloheptatrien-1-one, there was obtained 5-chloro-2-[4-(4-amino-6,7-dimethoxy-2-quinazolinyl)-1-piperazinyl]-2,4,6-cycloheptatrien-1-one (Ia: $R^3$=5-chloro-1-oxo-2,4,6-cycloheptatrien-2-yl; $R^4$, $R^5$, $R^6$ and $R^9$=H; $R^7$ and $R^8$=OMe and n=1); mp 202°–204° C. (crystallized from methanol-diethyl ether); ir (nujol mull) 3500, 3420, 3320, 3200 and 1245 cm$^{-1}$; uv max (MeOH) 350 ($\epsilon$=16500) and 250 nm ($\epsilon$=58200); nmr (DMSO-d$_6$) $\delta$ 3.4 (m, 4H), 3.75 and 3.80 (s, 6H) and 7.0 (6H); and Anal. Calcd for $C_{21}H_{22}ClN_5O_3$: C, 58.94% H, 5.14% N, 16.37% and Found: C, 58.91% H, 5.25% N, 16.48%.

EXAMPLE 4

2-[4-(2-Cycloheptimidazolyl)-1-piperazinyl]-6,7,8-trimethoxy-4-quinazolamine (Ia: $R^3$=2-cycloheptimidazolyl; $R^4$, $R^5$ and $R^6$=H; $R^7$, $R^8$ and $R^9$=OMe; and n=1)

A solution of 50 g of 3,4,5-trimethoxybenzoic acid in 500 ml dry methanol containing 4.8 ml of conc. sulfuric acid was refluxed under anhydrous condition for 18 hr and concentrated to half the volume. The solution was poured into ice water and extracted with methylene chloride. The organic extract was washed with cold 0.5 N sodium hydroxide and water, dried over sodium sulfate, evaporated and crystallized from hexane to give 3,4,5-trimethoxybenzoic acid methyl ester, mp 65°–66° C.

The latter ester (5 g) was dissolved in 25 ml of acetic anhydride and finely powdered cupric nitrate trihydrate (6 g) was added at a rate so that the internal temperature did not rise above 60° C. Thereupon the reaction mixture was left at room temperature for 1 hr and poured over ice. The precipitate was collected, washed, dried and crystallized from methylene chloride-hexane to give 3,4,5-trimethoxy-2-nitrobenzoic acid methyl ester, mp 65°–66° C. [this compound is described by K. I. H. Williams et al., J. Amer. Chem. Soc., 82, 3982 (1960)].

The latter nitro derivative (17.0 g) in 500 ml of methanol was reduced at room temperature and pressure with hydrogen using 4 g of 10% palladium on carbon as catalyst for 6 hr and filtered. The solvent was removed to give 14 g of 2-amino-3,4,5-trimethoxybenzoic acid methyl ester as an oil.

A solution of the latter amino ester (2.0 g) in a mixture of 7 ml of 2 N sodium hydroxide and 7 ml of methanol was refluxed for 10 min and concentrated to about half the volume under reduced pressure. The pH was adjusted to 5.5 with acetic acid. The resulting precipitate was filtered, washed with water, dried and crystallized from methylene chloride-hexane to give 2-amino-3,4,5-trimethoxybenzoic acid, mp 138°–140° C.

To a solution of the latter acid (1.3 g) in 5 ml of water and 1 ml of acetic acid, a solution of potassium cyanate (0.97 g) in 5 ml of water was added over a period of 15 min. The reaction was allowed to proceed for another 1.5 hr after which 7 g of sodium hydroxide pellets were added in portions. The reaction mixture was then heated at 90° C. for 0.5 hr, cooled and acidified with conc. hydrochloric acid. The resulting precipitate was collected, washed, air dried and crystallized from methanol to give 2,4-dihydroxy-6,7,8-trimethoxyquinazoline, mp>255° C. and Anal. Calcd for $C_{11}H_{12}N_2O_5$:C, 52.38% H, 4.80% N, 11.11% and Found: C, 52.30% H, 4.85% N, 11.01%.

A solution of the latter dihydroxy compound (8.4 g) in 50 ml of phosphorus oxychloride and 1.5 ml dimethyl aniline was refluxed for 4 hr, cooled and poured into ice water. The resulting precipitate was collected, air dried and crystallized from methylene chloride-hexane to give 2,4-dichloro-6,7,8-trimethoxyquinazoline, mp 149°-151° C. and nmr (CDCl$_3$) δ 4.02 (s, 3H), 4.11 (s, 3H), 4.12 (s, 3H) and 7.16 (1H).

Ammonia gas was bubbled through a solution of the latter dichloro compound (7.3 g) in 200 ml of dry tetrahydrofuran for 15 min. The solution was left at room temperature for 18 hr and evaporated. The resulting solids were suspended in water. The precipitate was filtered, washed with water, dried and crystallized from ethanol to obtain 4-amino-2-chloro-6,7,8-trimethoxyquinazoline, mp 244°-245° C.; nmr (DMSO-d$_6$) δ 3.88 (s, 6H), 3.94 (s, 3H), 7.44 (s, 1H) and 8.0 (s, 2H); and Anal. Calcd for $C_{11}H_{12}N_3O_3Cl$: C, 48.98% H, 4.45% N, 15.58% and Found: C, 49.14% H, 4.56% N, 15.67%.

A suspension of the latter compound (3.0 g) and 2-(1-piperazinyl)-cycloheptimidazole (4.5 g, described in Example 1) in 50 ml of butanol containing 3.5 g of triethylamine was refluxed with stirring for 4 hr, cooled, diluted with equal volume of ethanol and filtered. The yellow precipitate was suspended in water, filtered and dried to give 4.6 g of pure product. This product was crystallized from ethanol to give the title compound: mp 284°-285° C.; ir (nujol mull) 3360, 3300, 3180, 1695, 1610, 1573, 1532 cm$^{-1}$; uv max (MeOH) 253 nm (ε=64795); nmr (DMSO-d$_6$) δ 3.85 (s, 6H), 4.0 (m, 11H), 7.25 (s, 2H) and 7.8 (m, 6H); and Anal. Calcd for $C_{23}H_{25}N_7O_3$: C, 61.74% H, 5.59% N, 21.92% and Found: C, 61.82% H, 5.84% N, 21.84%.

EXAMPLE 5

2-[4-(6-Ethoxy-2-cycloheptimidazolyl)-1-piperazinyl]-6,7-dimethoxy-4-quinazolinamine (Ia: $R^3$=6-ethoxy-2-cycloheptimidazolyl; $R^4$, $R^5$, $R^6$ and $R^9$=H; $R^7$ and $R^8$=OMe; and n=1)

A solution of sodium (0.53 g) in ethanol (22 ml) was added over a period of 1 hr to a suspension of 2-[4-(6-chloro-2-cycloheptimidazolyl)-1-piperazinyl]-6,7-dimethoxy-4-quinazolinamine (2.6 g, described in Example 2). The resulting mixture was stirred at 20°-25° C. for 2 hr, refluxed for 1 hr, cooled and poured into water at 0° to 5° C. The precipitate was collected, washed with water, dried and chromatographed through silica gel using methanol-dichloromethane (1:9). The eluates were evaporated to give the title compound (1.18 g): mp >250° C.; ir (nujol) 3430, 3300 and 3170 cm$^{-1}$; uv max (Me OH) 214 (ε=27685), 253 (ε=70380), 275 (ε=38560), 370 (ε=38560) and 390 nm (ε=21950); nmr (DMSO-d$_6$) δ 1.4 (t, 3H), 3.9 (m, 14H), 6.75 (s, 1H), 7.17 (s, 2H), 7.4 (s, 1H), and 7.5–8 (m, 4H); and Anal. Calcd for $C_{24}H_{27}N_7O_3$: C, 62.46% H, 5.90% N, 21.24% and Found: C, 62.13% H, 6.01% N, 20.95%.

EXAMPLE 6

2-[4-(Benzthiazol-2-yl)-1-piperazinyl]-6,7-dimethoxy-4-quinazolinamine (Ia: $R^3$=benzthiazol-2-yl; $R^4$, $R^5$, $R^6$ and $R^9$=H; $R^7$ and $R^8$=OMe; and n=1)

A suspension of 2-(1-piperazinyl)-4-amino-6,7-dimethoxyquinazoline (1.96 g), 2-chlorobenzthiazole (1.02 g), triethylamine (1.82 g) in butanol (100 ml) was refluxed for 72 hr and filtered. The precipitate was taken up in a solution of methanol and dimethyl sulfoxide, and 1 N sodium hydroxide was added until the mixture was alkaline. The precipitate was collected, washed with water, dried (1.3 g) and crystallized from methanol to give the title compound: mp 242°-245° C.; ir (nujol) 3460 and 3370 cm$^{-1}$: uv max (MeOH) 227 (ε=4130), 250 (ε=5280), 276 (ε=3649) and 340 nm (ε=690); nmr (DMSO-d$_6$) δ 3.65 (m, 4H), 3.9 (m, 4H), 3.85 (s, 3H), 3.93 (s, 3H), 5.2 (s, 2H) and 7.2 (m, 6H); and Anal. Calcd for $C_{21}H_{22}N_6O_2S\cdot CH_3OH$: C, 58.14% H, 5.72% N, 18.50% and Found: C, 57.88% H, 5.90% N, 18.47%.

EXAMPLE 7

2-[4-(1,4,5,6,7,8-Hexahydrocycloheptimidazol-2-yl)-1-piperazinyl]-6,7-dimethoxy-4-quinazolinamine (Ia: $R^3$=1,4,5,6,7,8-hexahydrocycloheptimidazol-2-yl; $R^4$, $R^5$, $R^6$ and $R^9$=H; $R^7$ and $R^8$=OMe; and n=1)

A mixture of 2-[4-(2-cycloheptimidazolyl)-1-piperazinyl]-6,7-dimethoxy-4-quinazolinamine hydrochloride (1.0 g, described in Example 2) and 5% rhodium on carbon (0.10 g) in methanol (600 ml) was hydrogenated under an atmosphere of hydrogen at 50 lb/sq. in. pressure. The mixture was filtered and the filtrate was evaporated. The residue was dissolved in methanol and the solution was acidified with a few drops of 2 N hydrochloric acid. Acetone was added and crystals of the title compound were collected (0.880 g); mp>250° C.; ir (nujol) 3340 and 3160 cm$^{-1}$; uv max (MeOH) 250 (ε=56500), 330 (ε=8200) and 342 nm (ε=7850); and nmr (DMSO-d$_6$) δ 1.65 (m, 6H), 2.6 (m, 4H), 3.75 (m, 4H), 3.85 (s, 6H), 4.05 (m, 4H), 7.7 (s, 1H) and 7.75 (s, 1H).

EXAMPLE 8

2-[4-(2-Cycloheptimidazolyl)-1-piperazinyl]-6,7-dimethoxy-N-methyl-4-quinazolinamine (Ia: $R^3$=2-cycloheptimidazolyl; $R^4$=Me; $R^5$, $R^6$ and $R^9$=H; $R^7$ and $R^8$=OMe; and n=1)

To a solution of 2-chloro-4-amino-6,7-dimethoxyquinazoline (2.0 g) in tetrahydrofuran (100 ml), methylamine was introduced over a period of 15 min. The reaction mixture was stirred for 2 hr at room temperature and evaporated. The residue was triturated with cold aqueous sodium carbonate solution and the solid was washed and dried to give 1.769 g of 2-chloro-4-methylamino-6,7-dimethoxyquinazoline. A portion of this compound was crystallized from methylene chloride-hexane to mp 216°-217° C.; ir (nujol mull) 3470 cm$^{-1}$; nmr (DMSO-d$_6$) δ 3.0 (d, 3H), 3.9 (s, 6H), 7.05 (s, 1H), 7.55 (s, 1H) and 8.3 (broad s, 1H); and Anal. Calcd for $C_{11}H_{12}ClN_3O_2$: C, 52.07% H, 4.77% N, 16.56% and Found: C, 51.95% H, 4.70% N, 16.45%.

A mixture of 2-(1-piperazinyl)cycloheptimidazole hydrocloride (1.5 g, described in Example 1) and triethylamine (1.0 g) in butanol (150 ml) was stirred at room temperature for 15 min and 2-chloro-4-methylamino-6,7-dimethoxyquinazoline (1.53 g) was added. The mixture was refluxed for 22 hr, cooled and filtered. The precipitate was washed and dried to give 2.18 g of the title compound. This compound was dissolved in methanol and the solution was acidified with hydrogen chloride. The precipitate was collected, washed with diethyl ether and crystallized from water-methanol to obtain the dihydrochloride salt of the title compound: mp>250° C.; ir (nujol mull) 3000 cm$^{-1}$; uv max (MeOH) 345 (ε=22,000), 257 nm (ε=54,500) and 245 nm ($\epsilon$=55,200); nmr (DMSO-d$_6$) $\delta$ 3.07 (d, 3H), 3.88 (s, 6H), 4.18 (s, 8H) and 8.0 (s, 7H); and Anal. Calcd for C$_{23}$H$_{25}$N$_7$O$_2$.2HCl. ½ H$_2$O: C, 53.90% H, 5.46% N, 19.14% Cl, 13.86% and Found: C, 53.82% H, 5.68% N, 19.47% Cl, 13.1%.

EXAMPLE 9

2-[4-(2-Cycloheptimidazolyl)-1-piperazinyl]-5,6,7-trimethoxy-4-quinazolinamine (Ia: R$^3$=2-cycloheptimidazolyl; R$^4$, R$^5$ and R$^9$=H; R$^6$, R$^7$ and R$^8$=OMe; and n=1).

To a solution of 2,3,4-trimethoxybenzoic acid (25 g) in dry methanol (250 ml), concentrated sulfuric acid (2.4 ml) was added. The reaction solution was refluxed for 20 hr, concentrated to half its volume by evaporation, and poured into a mixture of ice and water. The solution was extracted with methylene chloride and the organic extract was washed with cold aqueous sodium carbonate solution and water, dried over sodium sulfate and evaporated to give 25.4 g of 2,3,4-trimethoxybenzoic acid, methyl ester: ir (CHCl$_3$) 1720 cm$^{-1}$; and nmr (CDCl$_3$) $\delta$ 3.85 (s, 3H), 3.87 (s, 3H), 3.92 (s, 6H), 6.65 (d, 1H) and 7.55 (d, 1H).

To a solution of the latter ester (1.0 g) in 3.8 ml of glacial acetic acid, 1.9 ml of concentrated nitric acid was added in drops taking care that the temperature of the mixture did not rise above 45° C. The reaction mixture was stirred at room temperature for 30 min and poured into a mixture of ice and water. The resulting precipitate was collected, washed and air dried to give 0.78 g of 2-nitro-4,5,6-trimethoxybenzoic acid, methyl ester which was crystallized from hexane-methylene chloride; mp 74°–76° C.; nmr (CDCl$_3$) $\delta$ 3.95 (s, 12H) and 7.5 (s, 1H); and Anal. Calcd for C$_{11}$H$_{13}$NO$_7$: C, 48.71% H, 4.83% N, 5.16% and Found: C, 48.68% H, 4.83% N, 5.05%.

A mixture of 20 g of the latter nitro ester in 250 ml of methanol and 2.0 g of palladium on carbon was hydrogenated under 40 psi for a period of 2.5 hr. The catalyst was filtered off and the filtrate was evaporated to give 1.6 g of 2-amino-4,5,6-trimethoxybenzoic acid, methyl ester which was crystallized from hexane-methylene chloride: mp 94°–96° C.; ir (CHCl$_3$) 3400, 3370 and 1675 cm$^{-1}$; uv max (MeOH) 326 ($\epsilon$=4420), 258 ($\epsilon$=8235) and 227 nm ($\epsilon$=26,280); nmr (CDCl$_3$)$\delta$ 3.57 (s, 3H), 3.80 (s, 3H), 3.88 (s, 6H) and 5.9 (s, 1H); and Anal. Calcd for C$_{11}$H$_{15}$NO$_5$: C, 54.75% H, 6.27% N, 5.81% and Found C, 54.74% H, 6.44% N, 5.66%.

To a solution of 14 g of the latter amino ester in 50 ml of methanol, 50 ml of 2 N sodium hydroxide was added. The mixture was refluxed for 2 hr, cooled and adjusted to pH 4 with acetic acid. The precipitate was collected by filtration, washed and dried to give 14 g of 2-amino-4,5,6-trimethoxybenzoic acid which was crystallized from hexane-methylene chloride: mp 88°–91° C.; ir (CHCl$_3$) 3490, 3340, 3160 and 1700 cm$^{-1}$; uv (max) 332 ($\epsilon$=4780), 259 ($\epsilon$=8455) and 230 nm ($\epsilon$=25,990); nmr (CDCl$_3$) $\delta$ 3.75 (s, 3H), 3.83 (s, 3H), 4.06 (s, 3H), 5.95 (s, 1H), 6.15 (2H) and 11.6 (1H); and Anal. Calcd for C$_{10}$H$_{13}$NO$_5$: C, 52.86% H, 5.77% N, 6.16% and Found: C, 52.96% H, 5.82% N, 6.07%.

To a stirred solution of 12 g of the latter amino acid in 500 ml of water containing 50 ml of acetic acid, 9.8 g of potassium cyanate in 90 ml of water was added in drops over a period of 15 min. The reaction mixture was stirred at room temperature for 18 hr, after which 11.4 g of sodium hydroxide pellets were added portionwise. The precipitate disappeared and the solution was heated at 90° C. for 0.5 hr, cooled and acidified with concentrated hydrochloric acid. The precipitate was collected, washed with water and dried to give 5.35 g of 2,4-dihydroxy-5,6,7-trimethoxyquinazoline, which was crystallized from ethanol: mp>250° C.; ir (nujol mull) 3140, 3000, 1725 and 1678 cm$^{-1}$; uv max (MeOH) 345 ($\epsilon$=20,730) and 250 nm ($\epsilon$=5,015); nmr (DMSO-d$_6$) $\delta$ 3.7 (s, 3H), 3.76 (s, 3H), 3.83 (s, 3H), 6.5 (s, 1H) and 10.75 (s, 2H); and Anal. Calcd for C$_{11}$H$_{12}$N$_2$O$_5$: C, 52.38% H, 4.80% N, 11.11% and Found: C, 52.39% H, 4.78% N, 11.13%.

A mixture of 5.5 g of the latter dihydroxy compound, 40 ml of phosphorus oxychloride and 1.2 ml of diethyl aniline was refluxed for 4 hr, cooled and carefully poured onto ice. The resulting precipitate was collected, washed with water and dried to give 3.3 g of 2,4-dichloro-5,6,7-trimethoxyquinazoline, which was crystallized from hexane-methylene chloride: mp 213°–215° C.; ir (CHCl$_3$) 1600 and 1535 cm$^{-1}$; uv max (MeOH) 326 ($\epsilon$=5,585), 254 ($\epsilon$=48,250) and 215 nm ($\epsilon$=21,765); nmr (CDCl$_3$) $\delta$ 4.0 (s, 3H), 4.1 (s, 6H) and 7.15 (s, 1H); and Anal. Calcd for C$_{11}$H$_{10}$N$_2$O$_3$Cl$_2$: C, 45.68% H, 3.48% N, 9.68% and Found: C, 45.50% H, 3.56% N, 9.66%.

To a solution of 3 g of the latter dichloro compound in 110 ml of dry tetrahydrofuran, dry ammonia was bubbled for a period of 15 min. The solution was stored at room temperature for 24 hr and filtered. The filtrate was evaporated to dryness. The residue after evaporation and the solids were suspended in water and filtered. The collected precipitate (2.2 g) was crystallized from ethanol to give 4-amino-2-chloro-5,6,7-trimethoxyquinazoline: mp 138°–140° C.; ir (nujol mull) 3460, 3260 and 3120 cm$^{-1}$; uv max (MeOH) 311 ($\epsilon$=5,165), 294 ($\epsilon$=5,165) and 283 nm ($\epsilon$=5,485); nmr (CDCl$_3$) $\epsilon$ 3.9 (s, 3H), 3.95 (s, 3H), 4.1 (s, 3H) and 6.42 (s, 1H); and Anal. Calcd for C$_{11}$H$_{12}$N$_3$O$_3$Cl: C, 48.98% H, 4.48% N, 15.58;1 % and Found: C, 48.88% H, 4.58% N, 15.55%.

A mixture of 2 g of 2-(1-piperazinyl)cycloheptimidazole hydrochloride (described in Example 1) and 3 g of triethylamine in 100 ml of butanol was stirred at room temperature for 15 min and 2 g of 2-chloro-4-amino-5,6,7-trimethoxyquinazoline (described above) was added. The solution was refluxed for 22 hr and evaporated to dryness under reduced pressure. The solids were triturated with water and the resulting precipitate was collected, washed and dried. The product (3.0 g) was purified by chromatography over silica gel using 7% methanol in methylene chloride as solvent. The appropriate fractions of the title compound were mixed, dissolved in acetone and hydrogen chloride gas was bubbled through the solution. The precipitate was collected and washed with acetone-diethyl ether to give 2.88 g of the dihydrochloride salt of the title compound, which was crystallized from methanol-diethyl ether: mp>250° C.; ir (KBr) 3420 cm$^{-1}$; uv max (MeOH) 285 ($\epsilon$=9330) and 253 nm ($\epsilon$=28,185); nmr (DMSO-d$_6$) $\epsilon$ 3.85 (s, 4H), 4.0 (s, 4H), 4.15 and 4.2 (s, 9H) and 7.15 (s, 1H) and Anal. Calcd for C$_{23}$H$_{25}$N$_7$O$_3$.2HCl.2H$_2$O: C, 49.64% H, 5.57% N, 17.62% Cl, 12.76% and Found: C, 49.67% H, 5.53% N, 17.60% Cl, 12.80%.

EXAMPLE 10

2-[4-(1H-2-Benzimidazolyl)-1-piperazinyl]-6,7-dimethoxy-4-quinazolinamine (Ia: $R^3$ = 1H-2-benzimidazolyl; $R^4$, $R^5$, $R^6$ and $R^9$ = H; $R^7$ and $R^8$ = OMe; and n = 1)

To 5.14 g of 4-amino-6,7-dimethoxy-2-(1-piperazinyl)quinazoline hydrochloride in 100 ml butanol, 11 ml of triethylamine was added. The mixture was stirred for 15 min and 2.65 g of 2-chloro-1H-benzimidazole was added. The mixture was refluxed for 18 hr and evaporated. Water was added to the residue and the residue was extracted with ethyl acetate. The ethyl acetate extract was washed with water, dried over sodium sulfate and evaporated. The residue was crystallized from methanol to give 3.5 g of the title compound, which was recrystallized from methanol: mp > 250° C.; ir (nujol mull) 3360 and 3180 cm$^{-1}$; uv max (MeOH) 341 ($\epsilon$ = 6,300), 284 ($\epsilon$ = 28,500) and 251 nm ($\epsilon$ = 66,800); nmr (DMSO-d$_6$) $\epsilon$ 3.5 (m, 4H), 3.8 (m, 4H), 3.8 (s, 3H), 3.84 (s, 3H), 7.1 (m, 8H) and 10.7 (s, 1H); and Anal. Calcd for $C_{21}H_{23}N_7O_2 \cdot \frac{1}{2} H_2O$: C, 60.86% H, 5.79% N, 23.67% and Found: C, 60.87% H, 5.98% N, 23.65%.

EXAMPLE 11

2-[4-(2-Benzoxazolyl)-1-piperazinyl]-6,7-dimethoxy-4-quinazolinamine (Ia: $R^3$ = 2-benzoxazolyl; $R^4$, $R^5$, $R^6$ and $R^9$ = H; $R^7$ and $R^8$ = OMe; and n = 1;1 )

To a suspension of 4-amino-6,7-dimethoxy-2-(1-piperazinyl)quinazoline hydrochloride (3.26 g) in 250 ml of butanol, 1.01 g of triethylamine was added. The mixture was stirred at room temperature for 2 hr and 1.51 g of benzoxazole-2-thiol was added. The mixture was refluxed for 72 hr and evaporated. The solids were triturated with water and filtered to give 2.7 g of crude product. This was chromatographed over silica gel using 7% methanol-methylene chloride as eluent. Appropriate fractions were mixed together to give 0.25 g of the title compound, which was crystallized from hexane-methylene chloride; mp > 250° C.; ir (nujol mull) 3420, 3320 and 3200 cm$^{-1}$; uv max (MeOH) 341 ($\epsilon$ = 6,650), 282 ($\epsilon$ = 28,900), 278 ($\epsilon$ = 29,300) and 252 nm ($\epsilon$ = 73,000); and Anal. Calcd for $C_{21}H_{22}N_6O_3$: C, 62.06% H, 5.45% N, 20.68% and Found: C, 61.38% H, 5.59% N, 20.78%.

We claim:
1. A compound of the formula

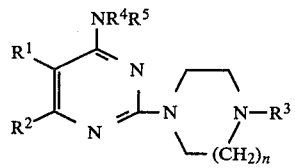

in which $R^1$ and $R^2$ are hydrogen, or $R^1$ and $R^2$ together form a chain of the formula

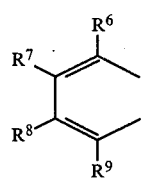

wherein $R^6$, $R^7$, $R^8$ and $R^9$ each is hydrogen or lower alkoxy; $R^3$ is selected from the group consisting of

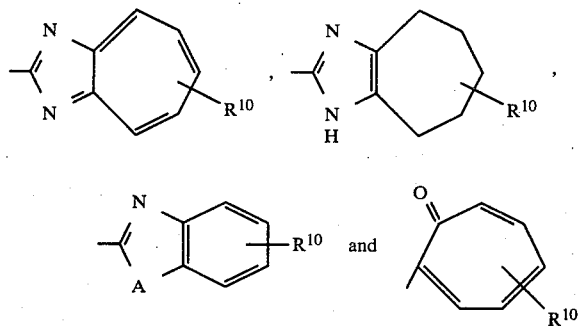

wherein $R^{10}$ is hydrogen, halo, lower alkyl, lower alkoxy, hydroxy, 1-oxo(lower)alkoxy or $NR^{11}R^{12}$ wherein $R^{11}$ and $R^{12}$ each is hydrogen or lower alkyl; A is O, S or NH; $R^4$ and $R^5$ each is hydrogen or lower alkyl; and n is 1 or 2; or a therapeutically acceptable acid addition salt thereof.

2. A compound of claim 1 of the formula

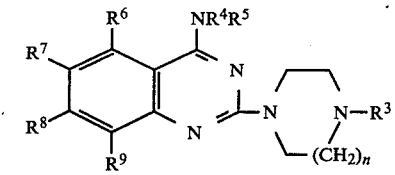

in which $R^4$, $R^5$ and $R^6$ are hydrogen, $R^7$ and $R^8$ each is lower alkoxy, $R^9$ is hydrogen or lower alkoxy, $R^3$ is selected from the group consisting of

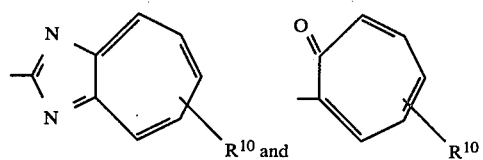

wherein $R^{10}$ is hydrogen, halo or lower alkoxy; and n is 1; or a therapeutically acceptable acid addition salt thereof.

3. A compound of claim 1 of the formula

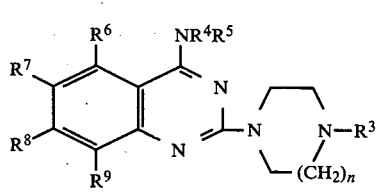

in which $R^4$, $R^5$ and $R^6$ are hydrogen, $R^7$ and $R^8$ each is lower alkoxy, $R^9$ is hydrogen or lower alkoxy, $R^3$ is selected from the group consisting of

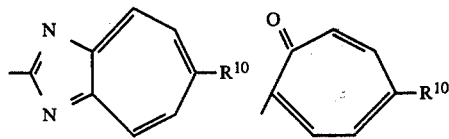

wherein R[10] is hydrogen, chloro or lower alkoxy; and n is 1; or a therapeutically acceptable acid addition salt thereof.

4. 2-[4-(2-Cycloheptimidazolyl)-1-piperazinyl]-6,7-dimethoxy-4-quinazolinamine, as claimed in claim 1.

5. 2-[4-(6-Chloro-2-cycloheptimidazolyl)-1-piperazinyl]-6,7-dimethoxy-4-quinazolinamine, as claimed in claim 1.

6. 2-[4-(2-Cycloheptimidazolyl)-1-piperazinyl]-4-pyrimidinamine, as claimed in claim 1.

7. 2-[4-(4-Amino-6,7-dimethoxy-2-quinazolinyl)-1-piperazinyl]-2,4,6-cycloheptatrien-1-one, as claimed in claim 1.

8. 5-Chloro-2-[4-(4-amino-6,7-dimethoxy-2-quinazolinyl)-1-piperazinyl]-2,4,6-cycloheptatrien-1-one, as claimed in claim 1.

9. 2-[4-(2-Cycloheptimidazolyl)-1-piperazinyl]-6,7,8-trimethoxy-4-quinazolinamine, as claimed in claim 1.

10. 2-[4-(6-Ethoxy-2-cycloheptimidazolyl)-1-piperazinyl]-6,7-dimethoxy-4-quinazolinamine, as claimed in claim 1.

11. 2-[4-(Benzthiazol-2-yl)-1-piperazinyl]-6,7-dimethoxy-4-quinazolinamine, as claimed in claim 1.

12. 2-[4-(1,4,5,6,7,8-Hexahydrocycloheptimidazol-2-yl)-1-piperazinyl]-6,7-dimethoxy-4-quinazolinamine, as claimed in claim 1.

13. 2-[4-(2-Cycloheptimidazolyl)-1-piperazinyl]-6,7-dimethoxy-N-methyl-4-quinazolinamine, as claimed in claim 1.

14. 2-[4-(2-Cycloheptimidazolyl)-1-piperazinyl]-5,6,7-trimethoxy-4-quinazolinamine, as claimed in claim 1.

15. 2-[4-(1H-2-Benzimidazolyl)-1-piperazinyl]-6,7-dimethoxy-4-quinazolinamine, as claimed in claim 1.

16. 2-[4-(2-Benzoxazolyl)-1-piperazinyl]-6,7-dimethoxy-4-quinazolinamine, as claimed in claim 1.

17. A pharmaceutical composition for treating hypertension, which comprises a compound of claim 1, and a pharmaceutically acceptable carrier therefor.

18. A method of treating hypertension in a hypertensive mammal, which comprises administering to said mammal an effective antihypertensive amount of a compound of claim 1.

* * * * *